(12) United States Patent
Lee

(10) Patent No.: US 7,642,405 B2
(45) Date of Patent: Jan. 5, 2010

(54) SWITCHABLE PHOTOSYSTEM-II DESIGNER ALGAE FOR PHOTOBIOLOGICAL HYDROGEN PRODUCTION

(76) Inventor: James Weifu Lee, 1123 Mortons Meadow Rd., Knoxville, TN (US) 37932

( * ) Notice: Subject to any disclaimer, the term of this patent is extended or adjusted under 35 U.S.C. 154(b) by 83 days.

(21) Appl. No.: 11/748,550

(22) Filed: May 15, 2007

(65) Prior Publication Data

US 2008/0127364 A1 May 29, 2008

Related U.S. Application Data

(60) Provisional application No. 60/801,126, filed on May 17, 2006.

(51) Int. Cl.
*C12N 15/63* (2006.01)
*C12N 15/82* (2006.01)

(52) U.S. Cl. ............... 800/296; 800/285; 800/286; 800/287

(58) Field of Classification Search ............... None
See application file for complete search history.

(56) References Cited

U.S. PATENT DOCUMENTS

| 6,989,252 | B2 | 1/2006 | Melis et al. | |
|---|---|---|---|---|
| 2005/0014239 | A1* | 1/2005 | Melis et al. | 435/168 |
| 2008/0120749 | A1* | 5/2008 | Melis et al. | 800/285 |

OTHER PUBLICATIONS

Lee J.W. et al., Appl. Biochem and Biotech. vol. 105-108 pp. 303-313.*
Dubertret G. Plant Physiology, 1981; vol. 67, pp. 47-53.*
E. Greenbaum, S. Blankinship, J. W. Lee, R. M. Ford (2001). "Solar photobiochemistry: Simultaneous photo-production of hydrogen and oxygen in a confined bioreactor," The Journal of Physical Chemistry B. 105:3605-3609.
Lee, J. W., and E. Greenbaum (2003) "A new oxygen sensitivity and its potential application in photosynthetic H2 production," Applied Biochemistry and Biotechnology, vol. 105-108, p. 303-313.
Ghiradi, M. L., R. K. Togasaki, and M. Seibert (1997) Appl. Biochem. Biotechnol. 63-65: 141-151.
Liszewski, K. (Jun. 1, 2003) Progress in RNA interference, Genetic Engineering News, vol. 23, No. 11, pp. 1-59.
Fire A, Xu S, Montgomery MK, Kostas SA, Driver SE, Mello CC (1998). "Potent and specific genetic interference by double-stranded RNA in *Caenorhabditis elegans*". Nature 391(6669):806-11.
Quinn, J. M., P. Barraco, M. Ericksson and S. Merchant (2000). "Coordinate copper- and oxygen-responsive Cyc6 and Cpx1 expression in *Chlamydomonas* is mediated by the same element." J Biol Chem 275: 6080-6089.
Kumada, Y., S. Hurinouchi, T. Uozumi, T. Beppu (1986) "Cloning of a streptomycin-production gene directing synthesis of N-methyl-L-glucosamine," Gene, 42:221-224.
Dykxhoorn DM, Novina CD, Sharp PA, "Killing the messenger: short RNAs that silence gene expression". Nat Rev Mol Cell Biol. Jun. 2003; 4(6):457-67.
Erickson, J. M. (1998). "Assembly of photosystem II" in the Molecular Biology of Chloroplast and Mitochondria in *Chlamydomonas*, ed. Rochaix, Clermont, and Merchant, Kluwer Academic Publishers, Boston, Chapter 15, pp. 255-285.
Ruffle, S. V. And R. T. Sayre (1998). "Functional analysis of photosystem II," in The Molecular Biology of Chloroplast and Mitochondria in *Chlamydomonas*, ed. Rochaix, Clermont, and Merchant, Kluwer Academic Publishers, Boston, Chapter 16, pp. 287-322.
Lee, James W., Stephen L. Blankinship and Elias Greenbaum (1995). "Temperature effect on production of hydrogen and oxygen by *Chlamydomonas* cold strain CCMP1619 and wild type 137c," Applied Biochemistry and Biotechnology 51/52:379-386.
Lee, James W., Laurens Mets, and Elias Greenbaum (2002). "Improvement of photosynthetic efficiency at high light intensity through reduction of chlorophyll antenna size," Applied Biochemistry and Biotechnology, 98-100: 37-48.
Buhrke, Thorsten, Oliver Lenz, Norbert Krauss, and Barbel Friedrich (2006) "Oxygen tolerance of the H2-sensing [NiFe] hydrogenase from *Ralstonia eutropha* H16, is based on limited access of oxygen to the active site," The Journal of Biological Chemistry, 280(25):23791-23796.
Jiao, D. M., and B. H. Ji (2001) "Photoinhibition in *indica* and *japonica* subspecies of rice and their reciprocal F-1 hybrids," Australian Journal of Plant Physiology, 28:299-306.
Patent Cooperation Treaty International Search Report (ISR) and Written Opinion (WO) mailed Oct. 03, 2008, for International Application No. PCT/US07/69065.

* cited by examiner

*Primary Examiner*—Russell Kallis
(74) *Attorney, Agent, or Firm*—Knox Patents; Thomas A. Kulaga

(57) ABSTRACT

A switchable photosystem-II designer algae for photobiological hydrogen production. The designer transgenic algae includes at least two transgenes for enhanced photobiological $H_2$ production wherein a first transgene serves as a genetic switch that can controls photosystem II (PSII) oxygen evolution and a second transgene encodes for creation of free proton channels in the algal photosynthetic membrane. In one embodiment, the algae includes a DNA construct having polymerase chain reaction forward primer (302), a inducible promoter (304), a PSII-iRNA sequence (306), a terminator (308), and a PCR reverse primer (310). In other embodiments, the PSII-iRNA sequence (306) is replaced with a $CF_1$-iRNA sequence (312), a streptomycin-production gene (314), a targeting sequence (316) followed by a proton-channel producing gene (318), or a PSII-producing gene (320). In one embodiment, a photo-bioreactor and gas-product separation and utilization system produce photobiological $H_2$ from the switchable PSII designer alga.

4 Claims, 8 Drawing Sheets

U.S. 7,642,405 B2

SEQUENCE LISTING

```
<160> NUMBER OF SEQ ID NOS: 3

<210> SEQ ID NO 1
<211> LENGTH: 967
<212> TYPE: DNA
<213> ORGANISM: Artificial Sequence
<220> FEATURE:
<223> OTHER INFORMATION: DNA Construct with OEE1-iRNA Sequence

<400> SEQUENCE: 1
agaaaatctg gcaccacacc gagctgtcat gcgttgttcc gttatgtgtc gtcaaacgcc      60
ttcgagcgct gcccggaaca atgcgtacta gtataggagc catgaggcaa gtgaacagaa     120
gcgggctgac tggtcaaggc gcacgatagg gctgacgagc gtgctgacgg ggtgtaccgc     180
cgagtgtccg ctgcattccc gccggattgg gaaatcgcga tggtcgcgca taggcaagct     240
cgcaaatgct gtcagcttat cttacatgaa cacacaaaca ctctcgcagg cactagcctc     300
aactcgagca tatgggcgtc cagggtgtag gtcaggcggg tcatgagctt ggtcttgaca     360
aactcagtct cgccaccctt gaactggctc tcctccttca cggtgaaaga ggtgggctca     420
```

-continued

```
atgcagaagt tctccagctt gtaggagccg gccttcagct ccttcaggtt ggtggtgccg      480
ctctccagca cggggcaggt gttggcaatg ccggagcccct tgacctgcag gtaggtcagg     540
ccctgaatct cgtcgaaggt cagggcgttg ccgacccgg caaccatggc ggtggccaga       600
gcagcggcag cggcggcctg ccgaccttc tgcgccttgc acaccacggc ggtggcacgg       660
ttgggccggg cggcacggac accgcctta cggactggg cagcgcggag gccattaat         720 ctagataaat ggaggcgctc gttgatctga gccttgcccc ctgacgaacg gcggtggatg      780
gaagatactg ctctcaagtg ctgaagcggt agcttagctc cccgtttcgt gctgatcagt      840 cttttcaac acgtaaaaag cggaggagtt ttgcaatttt gttggttgta acgatcctcc       900
gttgattttg gcctctttct ccatgggcgg gctgggcgta tttgaagcgg ttctctcttc      960
tgccgtt                                                                967
```

<210> SEQ ID NO 2
<211> LENGTH: 1652
<212> TYPE: DNA
<213> ORGANISM: Artificial Sequence
<220> FEATURE:
<223> OTHER INFORMATION: DNA construct with OEE1-iRNA sequence

<400> SEQUENCE: 2

```
agaaaatctg gcaccacacc gagctgtcat gcgttgttcc gttatgtgtc gtcaaacgcc       60
ttcgagcgct gcccggaaca atgcgtacta gtataggagc catgaggcaa gtgaacagaa      120
gcgggctgac tggtcaaggc gcacgatagg gctgacgagc gtgctgacgg ggtgtaccgc      180
cgagtgtccg ctgcattccc gccggattgg gaaatcgcga tggtcgcgca taggcaagct      240
cgcaaatgct gtcagcttat cttacatgaa cacacaaaca ctctcgcagg cactagcctc      300
aactcgagca tatggccctc cgcgctgccc agtccgctaa ggccggtgtc cgtgccgccc      360
ggtgagcagc atgcaatatt ttagcgtcga tactcggaaa ctataggagc gcatcagccg      420
accgatgttc gcgttgctgt cgcaggccca accgtgccac cgccgtggtg tgcaaggcgc      480
agaaggtcgg ccaggccgcc gctgccgctg ctctggccac cgccatggtt gccggggtga      540
gacactggat caaaacatcg cgcagcagca tcgggtgcca cagctcggcg atctaagctt      600
ggaatattgg acctggagga tctgcgcag cagcgagcgt tcggcggggt gctgcggggt       660
tcgcttgcga gcgacgacat ggcgctattt cgctaacgct tgctctcttg ctccctcccc      720
gtggatctgt gctcgcagtc ggccaacgcc ctgaccttcg acgagattca gggcctgacc      780
tacctgcagg tcaagggctc cggcattgcc aacctgccc cgtgctgga gagcggcacc       840 accaacctga aggagctgaa ggccggctcc tacaagctgg agaacttctg cattgagccc      900 acctcttttca ccgtgaagga ggagagccag ttcaagggtg gcgagactga gtttgtcaag      960
accaagctca tgacccgcct gacctacacc ctggacgccg gcgtccaggg tgtaggtcag     1020
gcgggtcatg agcttggtct tgacaaactc agtctcgcca cccttgaact ggctctcctc     1080
cttcacggtg aaagaggtgg gctcaatgca gaagttctcc agcttgtagg agccggcctt     1140
cagctccttc aggttggtgg tgccgctctc agcacggggg caggtgttgg caatgccgga     1200
gcccttgacc tgcaggtagg tcaggccctg aatctcgtcg aaggtcaggg cgttggccga     1260
cccggcaacc atggcggtgg ccagagcagc ggcagcggcg gcctggccga ccttctgcgc     1320
cttgcacacc acggcggtgg cacggttggg ccgggcggca cggacaccgg ccttagcgga     1380
ctgggcagcg cggagggcca ttaatctaga taaatggagg cgctcgttga tctgagcctt     1440
gccccctgac gaacggcggt ggatggaaga tactgctctc aagtgctgaa gcggtagctt     1500
```

-continued

```
agctccccgt tcgtgctga tcagtctttt tcaacacgta aaaagcggag gagttttgca    1560
attttgttgg ttgtaacgat cctccgttga ttttggcctc tttctccatg ggcgggctgg    1620
gcgtatttga agcggttctc tcttctgccg tt                                  1652
```

```
<210> SEQ ID NO 3
<211> LENGTH: 1289
<212> TYPE: DNA
<213> ORGANISM: Artificial Sequence
<220> FEATURE:
<223> OTHER INFORMATION: DNA construct with antisense OEE1-iRNA sequence

<400> SEQUENCE: 3
agaaaatctg gcaccacacc ataagggtca tagaatctag cgttatcctt ccacgagcgt      60
gtggcagcct gctggcgtgg acgagctgtc atgcgttgtt ccgttatgtg tcgtcaaacg     120
ccttcgagcg ctgcccggaa caatgcgtac tagtatagga gccatgaggc aagtgaacag     180
aagcgggctg actggtcaag gcgcacgata gggctgacga gcgtgctgac ggggtgtacc     240
gccgagtgtc cgctgcattc ccgccggatt gggaaatcgc gatggtcgcg cataggcaag     300
ctcgcaaatg ctgtcagctt atcttacatg aacacacaaa cactctcgca ggcactagcc     360
tcaaaccctc gaaacctttt tccaacagtt tacaccccaa ttcggacgcc gctccaagct     420
cgctccgttg ctccttcatc gcaccaccta ttatttctaa tatcgtagac gcgacaagat     480
ggccctccgc gctgcccagt ccgctaaggc cggtgtccgt gccgccggt gagcagcatg      540 caatatttta gcgtcgatac tcggaaacta taggagcgca tcagccgacc gatgttcgcg     600
ttgctgtcgc aggcccaacc gtgccaccgc cgtggtgtgc aaggcgcaga aggtcggcca     660
ggccgccgct gccgctgctc tggccaccgc catggttgcc ggggtgagac actggatcaa     720
aacatcgcgc agcagcatcg ggtgccacag ctcggcgatc taagcttgga atattggacc     780
tggaggatct ggcgcagcag cgagcgttcg gcggggtgct gcggggttcg cttgcgagcg     840
acgacatggc gctatttcgc taacgcttgc tctcttgctc cctccccgtg gatctgtgct     900
cgcaggcccg gcaaccatgg cggtggccag agcagcggca gcggcggcct ggccgacctt     960
ctgcgccttg cacaccacgg cggtggcacg gttgggccgg gcggcacgga caccggcctt    1020
agcggactgg gcagcgcgga gggccattaa atggaggcgc tcgttgatct gagccttgcc    1080
ccctgacgaa cggcggtgga tggaagatac tgctctcaag tgctgaagcg gtagcttagc    1140
tccccgtttc gtgctgatca gtcttttca acacgtaaaa agcggaggag ttttgcaatt     1200
ttgttggttg taacgatcct ccgttgattt tggcctcttt ctccatgggc gggctgggcg    1260
tatttgaagc ggttctctct tctgccgtt                                       1289
```

SWITCHABLE PHOTOSYSTEM-II DESIGNER ALGAE FOR PHOTOBIOLOGICAL HYDROGEN PRODUCTION

CROSS-REFERENCE TO RELATED APPLICATIONS

This Application claims the benefit of U.S. Provisional Application No. 60/801,126, filed on May 17, 2006.

STATEMENT REGARDING FEDERALLY SPONSORED RESEARCH OR DEVELOPMENT

This invention was made with Government support under Contract No. DE-AC05-00OR22725 awarded by the United States Department of energy. The Government has certain rights in this invention.

BACKGROUND OF THE INVENTION

1. Field of Invention

This invention pertains to a switchable photosystem-II (PSII) designer organism that is specifically designed for enhanced photobiological production of molecular hydrogen ($H_2$). The various embodiments include (1) application of a genetic switch that can control the expression of PSII activity for production of $H_2$ without $O_2$ production and (2) combination of switchable PSII with programmable proton channels in algal photosynthetic membrane that further enhance photobiological $H_2$ production. In particular, this invention pertains to a switchable PSII designer alga for enhanced photobiological $H_2$ production. Various embodiments solves the following six major problems that currently challenge those in the field of photobiological $H_2$ production: (1) drainage of electrons by $O_2$, (2) poisoning of the hydrogenase enzyme by $O_2$, (3) the mixed $H_2$ and $O_2$ gas-product separation and safety issues, (4) restriction of photosynthetic $H_2$ production by accumulation of a proton gradient, (5) competitive inhibition of photosynthetic $H_2$ production by $CO_2$, and (6) requirement for bicarbonate binding at photosystem II (PSII) for efficient photosynthetic activity.

2. Background

Algal (such as *Chlamydomonas reinhardtii*, *Platymonas subcordiformis*, *Chlorella fusca*, *Ankistrodesmus braunii*, and *Scenedesmus obliquus*) photosynthetic hydrogen ($H_2$) production from water has tremendous potential to be a clean and renewable energy resource. As shown in FIG. 1, in the algal system, $H_2$ is produced through hydrogenase-catalyzed reduction of protons by the electrons generated from photosynthetic oxidation of water using sunlight energy. The net result is photoevolution of $H_2$ and $O_2$ from water ($H_2O$). However, there are a number of technical issues that must be addressed before algal $H_2$ production can become practical. The following lists the six technical problems that currently challenge researchers and investors in the field of photosynthetic $H_2$ production: (1) drainage of electrons by $O_2$, (2) poisoning of the hydrogenase enzyme by $O_2$, (3) the mixed $H_2$ and $O_2$ gas-product separation and safety issues, (4) restriction of photosynthetic $H_2$ production by accumulation of a proton gradient, (5) competitive inhibition of photosynthetic $H_2$ production by $CO_2$, and (6) requirement for bicarbonate binding at photosystem II (PSII) for efficient photosynthetic activity.

Of these six technical problems in the wild-type organism, the first three are all oxygen-related issues that must be solved in order for the algal $H_2$-production technology to work. Here is the reason why the three oxygen-related issues must be solved in order for the algal $H_2$-production technology to work well. In wild-type algae as illustrated in FIG. 1, photosynthetic water splitting under anaerobic condition can result in simultaneous production of $H_2$ and $O_2$ in the same cell. Therefore, the gas products in this case are a dangerous mixture of $H_2$ and $O_2$ that requires safe separation (problem 3). Furthermore, the $O_2$ produced in the alga can inhibit $H_2$ production by two mechanisms: acting as an electron acceptor [possibly through the RuBisco (which is also a known oxygenase) enzyme at the Calvin cycle] that drains the electrons away from the Fd/hydrogenase $H_2$ production pathway (problem 1), and poisoning the hydrogenase enzyme directly (problem 2).

The inhibition of algal $H_2$ production by $O_2$ is a serious problem that can be measured experimentally. As shown in the experimental data presented in FIG. 2, an introduction of merely 0.1000% $O_2$ (equivalent to 1000 ppm $O_2$) results in a dramatic inhibition on the $H_2$-production rate of the wild-type alga *C. reinhardtii*. The steady-state $H_2$-production rate in the presence of 1000 ppm $O_2$ was 0.33 μmol of $H_2$/mg Chl/hr, which is only about 2.8% (less than a $30^{th}$) of the full steady-state rate (12 μmol of $H_2$/mg Chl/hr) before the introduction of the 0.1000% $O_2$. Therefore, it is not practical to use the wild-type alga for production of $H_2$ and $O_2$ by photosynthetic water splitting. In order to realize the full potential of the algal $H_2$-production mechanism, these oxygen-related problems must be solved.

The various embodiments overcome these three oxygen-related problems for enhanced $H_2$ production in an effective way by creating a designer alga that contains switchable PSII reaction centers for production of pure $H_2$ without $O_2$ production. Use of the designer switchable PSII algae in conjunction with the features of my designer proton-channel algae represents a significant photobiological $H_2$-production technology in the field of renewable energy production. The application titled "Designer proton-channel transgenic algae for photobiological hydrogen production" and filed on the same day and by the same inventor as this application is hereby incorporated by reference in its entirety. There are other approaches reported in the field of studies such as the "sulfur-deprivation"-based approach that are also attempted to solve the $O_2$-related problems. The various embodiments are distinguished from the prior art by its innovative application of the emerging RNA interference technique with a genetic switch to selectively (and switchably) suppress PSII oxygen-evolution activity and create free proton channels in algal photosynthetic membrane. It provides a unique solution to both the oxygen-related problems and the proton-gradient-related issues for enhanced photobiological $H_2$ production. For example, the "sulfur-deprivation"-based physiological approach is not required here at all. With its features of switchable genetic expression of both PSII and proton channel in algal photosynthetic membrane, the designer alga can be used to solve all of the listed six problems that currently challenge researchers and investors in the field of photobiological $H_2$ production.

BRIEF SUMMARY OF THE INVENTION

In accordance with various embodiments, there are provided designer transgenic algae comprising at least two transgenes for enhanced photobiological $H_2$ production wherein a first said transgene serves as a genetic switch that controls photosystem II (PSII) oxygen evolution and a second said transgene encodes for creation of free proton channels in algal photosynthetic membranes, such as thylakoid membrane. The switchable PSII designer algae, combined with the benefits of programmable creation of free proton channels in algal photosynthetic membranes, provides an effective new solution for efficient and robust photobiological $H_2$ production, by solving all the six major problems that currently challenge those in the field of photosynthetic $H_2$ production.

The various embodiments teach how to create the switchable PSII designer algae combined with creation of free proton channels in algal photosynthetic membranes. In one embodiment, the switchable PSII designer feature is accomplished by creation and use of a genetically transmittable factor that inducibly controls the expression of PSII oxygen-evolving activity. The newly-emerging interference RNA technique is applied in creating and using a piece of designer PSII interfering RNA (iRNA) to programmably suppress the expression of PSII oxygen-evolving activity to solve the three $O_2$-related problems in relation to algal $H_2$ production. When the genetic background of a PSII deficient mutant is employed, such as the use of a PSII deletion mutant, as a host organism to create the designer algae, a designer PSII (e.g., OEE1) producing gene that inducibly complements the corresponding PSII (e.g., OEE1) deficiency is used also as a genetic switch to control the PSII oxygen-evolution activity. Meanwhile, inducible creation of free proton channels in algal photosynthetic thylakoid membranes is also described with innovative application of a designer CF1-iRNA gene in addition to targeted genetic insertion of designer polypeptide proton channels with synthetic genes.

In one embodiment, the switchable PSII designer algae are used with a photo-bioreactor and gas-product separation and utilization system for enhanced photobiological $H_2$ production. The various embodiments effectively provide a single-organism (switchable PSII designer alga) two-stage $H_2$-production technology. In various embodiments, organic reserve, such as starch, is accumulated through photoautotrophic algal culture growth by normal oxygenic photosynthesis using $CO_2$ and sunlight energy in an aerobic reactor. When the algal culture is grown and significant amounts of organic reserves are accumulated in the designer alga cells, the culture is placed under anaerobic conditions to express the designer genes to shut off PSII oxygen evolution and create proton channels in algal thylakoid membrane so that the algae will produce $H_2$ by the metabolic (dark) and photosystem I (PSI)-driven (light) $H_2$ production pathways without production of $O_2$. The source of electrons for the metabolic and PSI-driven $H_2$ production is organic reserves such as starch that are made in the previous cycle of oxygenic photosynthetic $CO_2$ fixation. Since the gas product is essentially pure $H_2$ and $CO_2$ without $O_2$ because of the inactivation of PSII $O_2$-evolution activity, an $O_2$-free condition in an algal bioreactor is easily maintained for $H_2$ production and all of the $O_2$-related problems are thus eliminated along with the elimination of the proton-gradient-related problems by a proton channel. The net result is the production of hydrogen and oxygen from water. The maximal theoretical sunlight-to-$H_2$ energy conversion efficiency for this designer alga-two-stage $H_2$-production process is about 5%.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

In accordance with various embodiments, there are provided designer transgenic algae comprising two transgenes (FIGS. 3A and 3B) for enhanced photobiological $H_2$ production wherein a first said transgene serves as a genetic switch that controls photosystem II (PSII) oxygen evolution and a second said transgene encodes for creation of free proton channels in algal photosynthetic membranes, such as thylakoid membrane.

Figure 1:
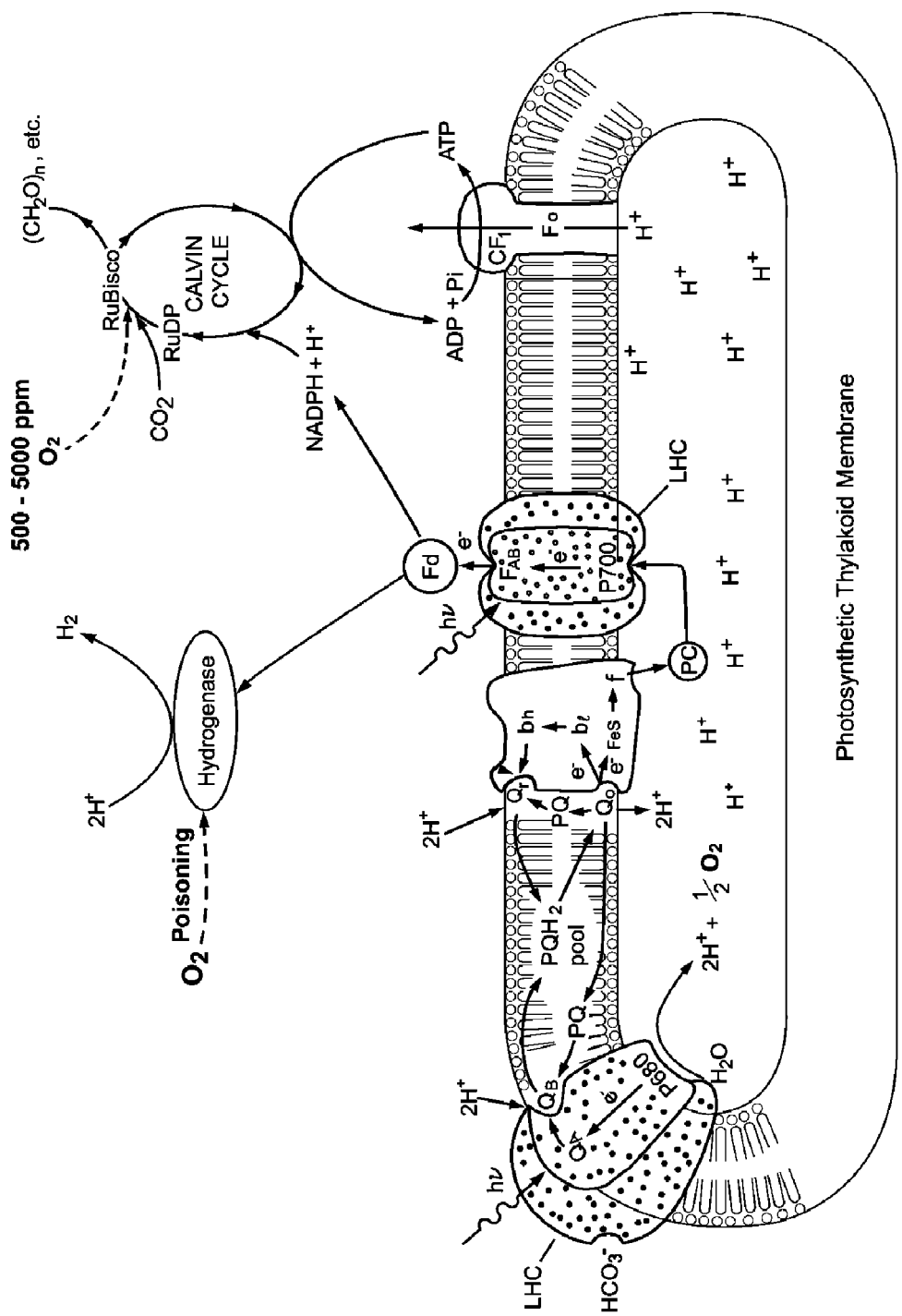
FIG. 1 illustrates photosynthetic $H_2$ production pathway in wild-type alga such as *Chlamydomonas reinhardtii*.
Figure 2:
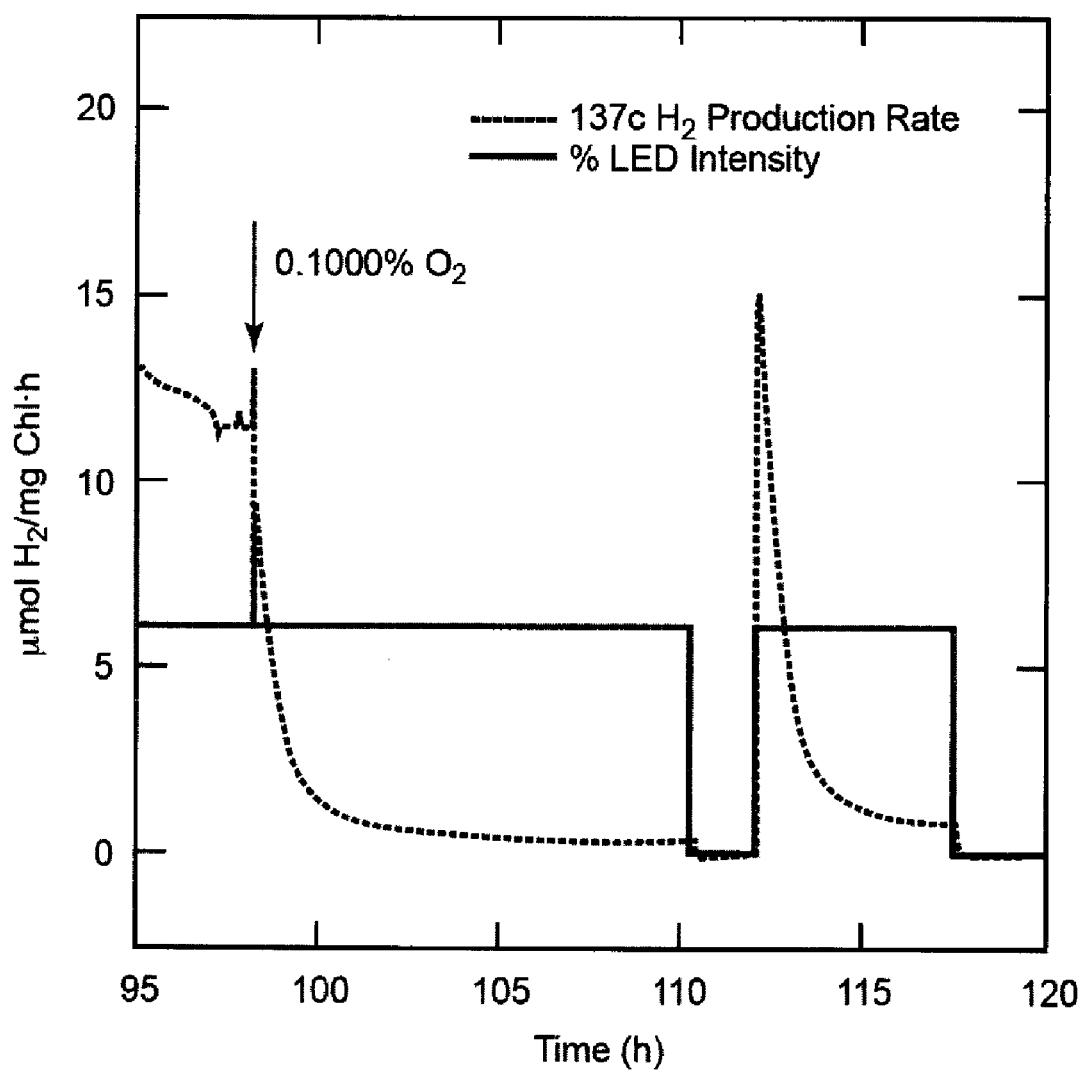
FIG. 2 presents a typical wild-type algal $H_2$-production curve showing its sensitivity to $O_2$.
Figure 3A:
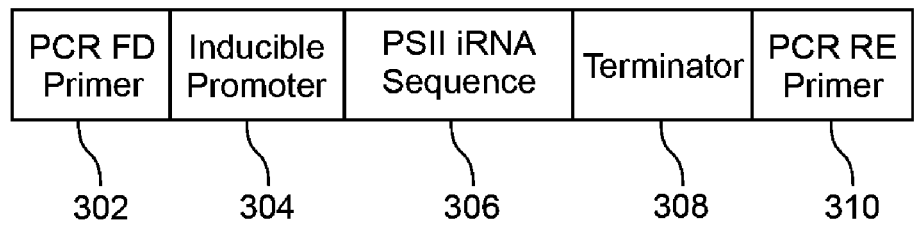
FIG. 3A illustrates one embodiment of a DNA construct of a switchable photosystem II (PSII) suppressor gene.

In one embodiment, the switchable PSII designer alga is created by transformation of a host alga with at least one DNA construct 300-A as shown in FIG. 3A that contains a designer PSII suppressor gene linked with an externally inducible promoter such as a redox-condition-sensitive hydrogenase promoter serving as a genetic switch. According to this embodiment, the designer PSII suppressor is a PSII iRNA that can specifically suppress PSII oxygen evolution activity. The general design of the PSII suppressor gene is shown in its DNA construct 300-A, which comprises the following components: a) a polymerase chain reaction forward (PCR FD) primer 302; b) an externally inducible promoter 304; c) a PSII-iRNA sequence 306; d) a transcription terminator 308; and e) a PCR reverse (RE) primer 310.

Figure 3B:
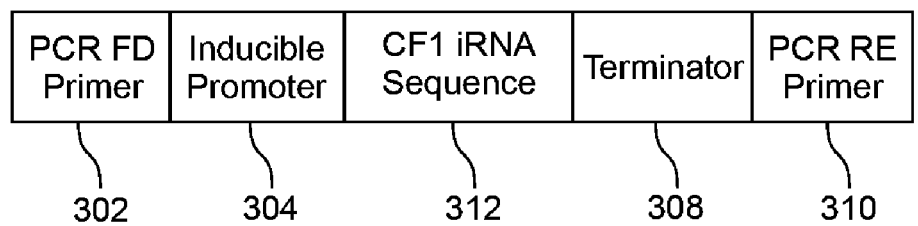
FIG. 3B illustrates another embodiment of a DNA construct of a designer $CF_1$ suppressor gene.

A second transgene, illustrated in FIG. 3B, that encodes an inducible $CF_1$-iRNA is added also into genome of the designer alga to create free $CF_0$ proton channels in algal photosynthetic membranes by suppressing the expression of $CF_1$ along with the suppression of PSII and the induction of the hydrogenase under certain specific conditions, such as the anaerobic conditions. The general design of the DNA construct 300-B for the $CF_1$ suppressor gene is shown in FIG. 3B, which includes the following components: a) a polymerase chain reaction (PCR) forward (FD) primer 302; b) an externally inducible promoter 304; c) a $CF_1$-iRNA sequence 312; d) a transcription terminator 308; and e) a PCR reverse (RE) primer 310.

In various embodiments, the components a) through e) 302, 304, 306, 308, 310, 312 of the DNA constructs 300-A, 300-B are adjusted to suit for certain specific conditions. In practice, any of the components a) through e) 302, 304, 306, 308, 310 of these DNA constructs 300-A are applied in full or in part, and/or in any adjusted combination as well to achieve more desirable results.

Figure 3C:
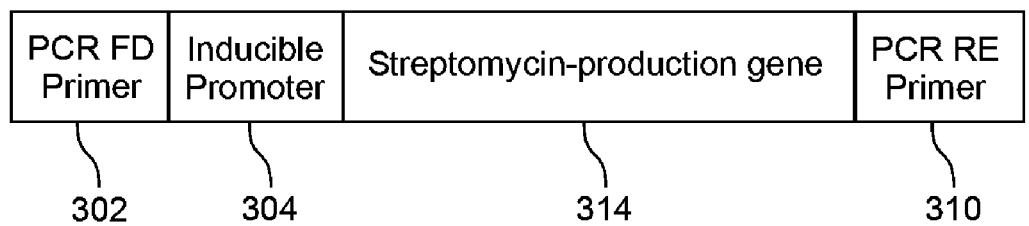
FIG. 3C illustrates another embodiment of a DNA construct of a designer PSII inhibitor gene.
Figure 3D:
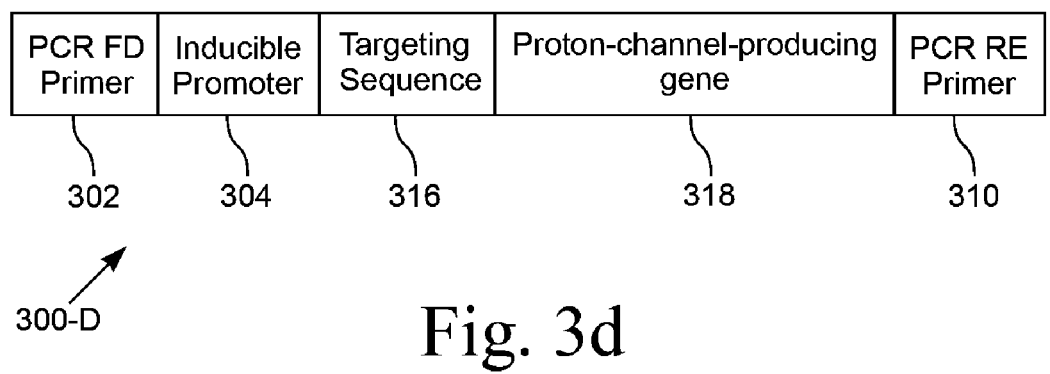
FIG. 3D illustrates another embodiment of a DNA construct of a designer proton-channel-producing gene.
Figure 3E:
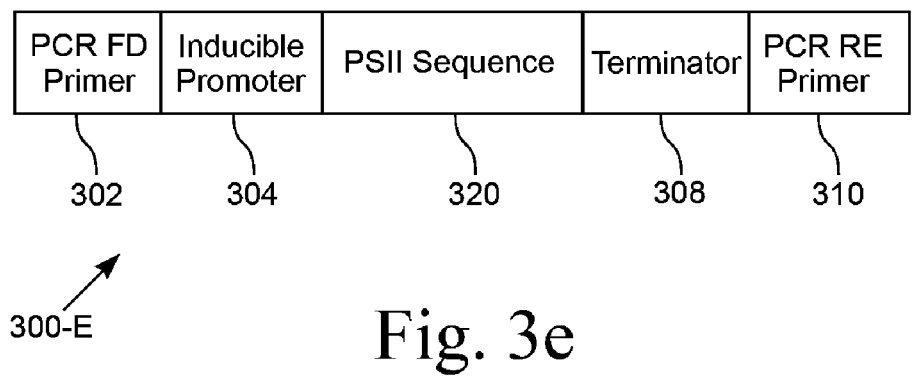
FIG. 3E illustrates another embodiment of a DNA construct of a designer PSII-producing gene.
Figure 4A:
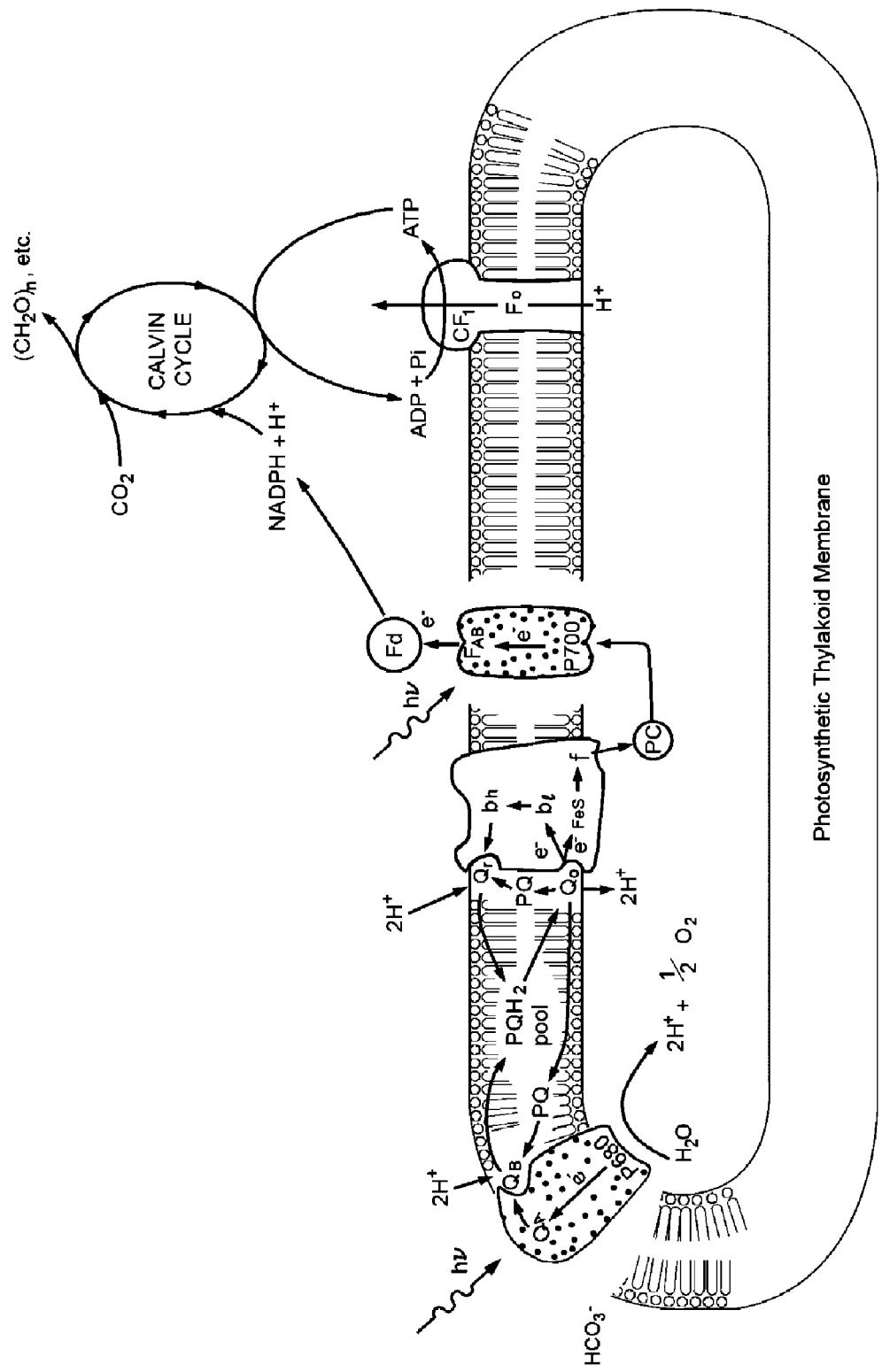
FIG. 4A illustrates the switchable-PSII designer alga capable of growing photoautotrophically and accumulating starch through oxygenic photosynthesis using ambient-air $CO_2$ under aerobic conditions such as in an aerobic reactor or open pond.

Hydrogenase promoter is an anaerobic inducible promoter that serves as a genetic switch to desirably control the expression of the designer transgenes (FIGS. 3A-3D). Therefore, the designer transgenes can be expressed only under certain specific conditions, such as the anaerobic conditions. Under aerobic conditions, the designer transgenes are normally not expressed, except for the designer PSII-producing gene illustrated in FIG. 3E. Consequently, as illustrated in FIG. 4A, the switchable PSII designer alga performs autotrophic photosynthesis using ambient-air $CO_2$ as the carbon source and grows normally, just like a wild-type organism under aerobic conditions, such as in an open pond. When the algal culture is grown and ready for $H_2$ production (when sufficient amounts of starch are accumulated through the normal oxygenic photosynthetic fixation of $CO_2$), the algal cells are placed under anaerobic conditions to express the designer transgenes simultaneously with the induction of the hydrogenase enzyme because of the use of the hydrogenase promoter.

Figure 4B:
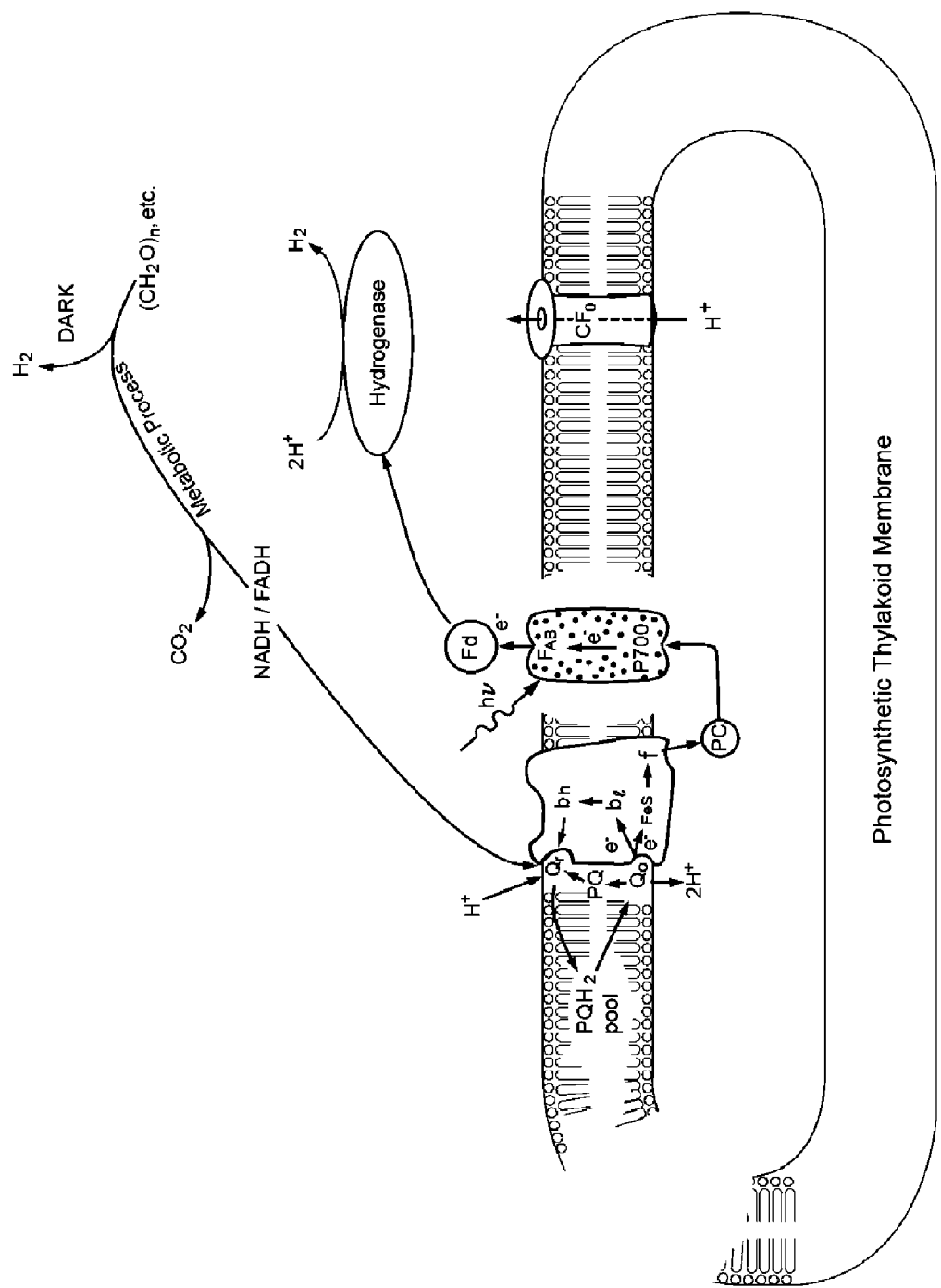
FIG. 4B illustrates the photobiological $H_2$ production pathway in a switchable-PSII designer alga when the designer PSII-iRNA (and/or PSII-inhibitor such as streptomycin) gene and the designer $CF_1$-iRNA gene are expressed upon induction of the hydrogenase.

As illustrated in FIG. 4B, the expression of the PSII inhibitor gene (as illustrated in FIG. 3A) will shut off PSII $O_2$ evolution so that the alga will produce $H_2$ by the metabolic (dark) and PSI-driven (light) $H_2$ production pathways without production of $O_2$. The source of electrons for the metabolic and PSI-driven $H_2$ production is organic reserves, such as starch (as illustrated in FIG. 4B) that are made in the previous cycle of oxygenic photosynthetic $CO_2$ fixation (FIG. 4A). Since the gas product in the embodiment illustrated in FIG. 4B is essentially pure $H_2$ and $CO_2$ without $O_2$, the problems of $H_2$ and $O_2$ mixture (including problems 1-3: drainage of electrons by $O_2$, poisoning of the hydrogenase enzyme by $O_2$, and the gas-separation and safety issues) are eliminated with the designer algae.

According to one embodiment, use of a proton channel in the algal photosynthetic thylakoid membrane also enhances this mode of PSI-driven $H_2$ production from organic reserves. As illustrated in FIG. 4B, operation of the PSI-driven $H_2$-production mechanism results in translocation of protons across the thylakoid membrane from the stroma into the lumen as the reducing power (NADH, NADPH, FADH) from degradation of organic reserves enters the PQ pool near the $Q_r$ site of Cyt b/f complex and is then oxidized at the $Q_o$ site. If a free proton-conducting channel is not present in the thylakoid membrane, protons could accumulate at the lumen (inside the thylakoids) and impede the electron transport for this PSI-driven $H_2$ production. Furthermore, the presence of a free proton-conducting channel in algal thylakoid membrane will ensure the inactivation of the Calvin-cycle activity that could compete with the Fd/hydrogenase $H_2$-production pathway for the electrons derived from the PSI-driven decomposition of the organic reserves. Therefore, in one embodiment it is a practice to incorporate the benefits of a programmable thylakoid proton channel into the switchable-PSII designer alga. This embodiment is achieved by delivery of a $CF_1$-suppressor transgene 312, as illustrated in FIG. 3B, also into the genome of the designer alga to create free $CF_o$ proton channels in algal photosynthetic membranes by inhibiting the expression of $CF_1$ with a $CF_1$-iRNA that the $CF_1$-suppressor transgene can produce under the anaerobic conditions upon the induction of the hydrogenase along with the suppression of PSII-oxygen-evolving activity.

Therefore, the co-expression of the PSII suppressor 306, the $CF_1$ suppressor 312, and hydrogenase makes this alga a more efficient and robust system for production of $H_2$. This organism contains normal mitochondria, which can use the reducing power (NADH) from organic reserves (and/or exogenous substrates such as acetate) to power the cell immediately after its return to aerobic conditions. Therefore, when the algal cell is returned to aerobic conditions after its use under anaerobic conditions for production of $H_2$, the cell will stop generating non-functional PSII in thylakoid membranes and start to restore its normal photoautotrophic capability by synthesizing functional thylakoids. Consequently, it is possible to use this type of genetically transformed organism for repeated cycles of photoautotrophic culture growth (starch accumulation) under normal aerobic conditions (FIG. 4A) and efficient production of $H_2$ under anaerobic conditions (FIG. 4B).

One aspect is the innovative application of a genetic switch to control the expression of PSII activity for production of $H_2$ without the three $O_2$ problems (illustrated in FIGS. 4A and 4B). This switchability is accomplished through application of an externally inducible promoter such as a hydrogenase promoter. To function as intended, the designer transgenes (FIGS. 3A-3D) must be inducibly expressed under anaerobic conditions. In one embodiment, an algal hydrogenase promoter, such as the promoter of the hydrogenase gene (Hyd1) of *Chlamydomonas reinhardtii*, is used as an effective genetic switch to control the expression of the designer genes to the exact time and conditions where they are needed for enhanced photobiological $H_2$ production as illustrated in FIG. 4B. That is, the designer transgenes will be synthesized only at the time when the hydrogenase is induced and ready for $H_2$ production under anaerobic conditions. Therefore, the hydrogenase promoter can be employed as an inducible promoter for each of the DNA constructs 300-A, 300-B, 300-C, 300-D to serve as a genetic switch to control the expression of the designer genes. The reason that the designer alga can perform autotrophic photosynthesis using $CO_2$ as the carbon source under aerobic condition (illustrated in FIG. 4A) is because the designer genes (illustrated in FIGS. 3A, 3B, 3C, 3D) are not expressed under aerobic conditions owing to the use of a hydrogenase promoter, which can be turned on only under the anaerobic conditions when needed for photobiological $H_2$ production.

In addition to the hydrogenase promoter, there are other promoters that can also be used to construct the desired genetic switch for designer genes (FIGS. 3A, 3B, 3C, 3D). *Chlamydomonas* cells contain several nuclear genes that are coordinately induced under anaerobic conditions. These include the hydrogenase structural gene itself (Hyd1), the Cyc6 gene encoding the apoprotein of Cytochrome $C_6$, and the Cpx1 gene encoding coprogen oxidase. The regulatory regions for the latter two have been well characterized, and a region of ~100 bp proves sufficient to confer regulation by anaerobiosis in synthetic gene constructs. The promoter strengths of these three genes vary considerably; each may thus be selected to control the expression levels of the designer genes (FIGS. 3A, 3B, 3C, 3D) for enhanced photobiological production of $H_2$. There are a number of other regulated promoters that can also be used and/or modified to serve as the genetic switches. For example, the nitrate reductase (Nia1) promoter which is induced by growth in nitrate medium and repressed in nitrate-deficient but ammonium-containing medium can be used to control the expression of certain designer genes, such as the designer PSII-producing gene 300-E illustrated in FIG. 3E, according to the concentration levels of nitrate in a culture medium as well. Therefore, inducible promoters that can be used and/or modified to serve for this purpose include, but are not limited to, hydrogenase promoters, Cytochrome $C_6$ (Cyc6) promoter, Nia1 promoter, CabII-1 promoter, Ca1 promoter, Ca2 promoter, coprogen oxidase promoter, and/or their analogs and modified designer sequences. Use of these externally inducible promoters can also create varieties of designer algae.

The PSII-iRNA DNA sequence 306 (FIG. 3A) and the CF1-iRNA DNA fragment 312 (FIG. 3B) are artificially designed based on the principle of the emerging RNA interference technique. The RNA interference technique uses a piece of interfering RNA (iRNA) that can specifically bind with the mRNA of a particular gene, thus inhibiting (suppressing) the translation of the gene-specific mRNA to protein. Inactivation of PSII oxygen evolution activity is achieved by suppressing the expression of any key PSII components including its OEE1, D1, CP47, CP43, or D2 protein subunits. Therefore, the envisioned PSII iRNA further includes, but is not limited to, OEE1 iRNA, D1 iRNA, CP47 iRNA, CP43 iRNA and/or D2 iRNA. For example, the OEE1 subunit is a key component of the PSII oxygen-evolving complex (OEC) that is directly responsible for the oxygen evolution process. It is conceivable that deletion (suppression by an OEE1-specific iRNA) of the OEE1 subunit results in an OEE1-deficient PSII that is no longer able to evolve molecular oxygen by oxidation of water. The gene that encodes for the OEE1 subunit is PsbO (also known as Psb1), which is a nuclear DNA that can be used with the hydrogenase promoter. Therefore, an anti-sense OEE1 DNA can be designed for generation of an anti-sense mRNA (iRNA) that can inhibit the synthesis of the OEE1 subunit by binding with the normal OEE1 mRNA. Unlike in the mammalian systems, where 21-nt probes are often used to target mRNA for inhibition, the iRNA in microbes (including the host organism *Chlamydomonas reinhardtii*) can be longer segments to be more gene-specific. It is one practice to consider the following three criteria in designing the DNA sequence of the PSII suppressor (such as OEE1 iRNA): (a) the iRNA is a contiguous segment of the PSII subunit (e.g., OEE1) mRNA, typically with a length range of about 20-1200 base pairs; (b) the iRNA is specific to the PSII subunit (e.g., OEE1), i.e., any significant portion of the iRNA does not have high sequence identity to part of an RNA of any other genes in the host organism such as *Chlamydomonas reinhardtii*; (c) the iRNA does not have significant self complimentarity to form stable secondary structure that prevents hybridization with the PSII subunit (e.g., OEE1) mRNA. Because such a designed DNA fragment does not have any significant sequence similarity to other known genes, it (when transformed into the host alga) is able to produce an iRNA that specifically binds with normal mRNA of OEE1 thus selectively inhibiting the translation of the OEE1 mRNA into its protein. The $CF_1$-iRNA sequence 312 is designed with similar principles. Therefore, the iRNA technique can be applied in conjunction with an inducible promoter, such as the hydrogenase promoter, as a genetic switch to create a desirable switchable-PSII designer alga for improved photobiological $H_2$ production.

In the embodiments illustrated in FIGS. 3A and 3B, each of the designer-suppressor DNA constructs 300-A, 300-B also contains a terminator 308 after the designer suppressor encoding sequence. The terminator DNA sequence 308, which is designed based on the sequences of natural gene terminators, is to ensure that the transcription of said designer gene is properly terminated to produce an exact designer iRNA as desired.

Each of the two DNA constructs 300-A, 300-B shown in FIGS. 3A and 3B includes a pair of polymerase chain reaction (PCR) primers: a PCR forward primer (PCR FD primer) 302 and a PCR reverse primer (PCR RE primer) 310 located respectively at the beginning (the 3' end) and at the other end of said DNA construct 300-A, 300-B. This pair of PCR primers 302, 310 is designed to provide certain convenience when needed for relatively easy PCR amplification of a given designer DNA construct 300, which is helpful not only during and after the designer DNA construct 300 is synthesized in preparation for gene transformation, but also after the designer DNA construct 300 is delivered into the genome of a host alga for verification of the designer transgene in the transformants. For example, after the transformation of the designer gene is accomplished in a *Chlamydomonas reinhardtii*-arg7 host cell using the techniques of electroporation and argininosuccinate lyase (arg7) complementation screening, the resulting transformants are analyzed by a PCR DNA assay of their nuclear DNA using this pair of PCR primers 302, 310 to verify whether the entire DNA construct 300-A of FIG. 3A is successfully incorporated into the genome of a given transformant. When the nuclear DNA PCR assay of a transformant can generate a PCR product that matches with the predicted DNA size and sequence according to the designer DNA construct 300-A, the successful incorporation of the designer gene (DNA construct) into the genome of the transformant is verified.

Therefore, the various embodiments also teach the associated method to effectively create the designer transgenic alga for photobiological $H_2$ production. This method, in one embodiment, includes the following steps: a) Selecting appropriate host algae with respect to their genetic backgrounds and special features in relation to $H_2$ production; b) Genetically deleting any $H_2$-consuming activities such as the uptake-hydrogenase activities in the selected host algae; c) Introducing the nucleic acid constructs of the designer genes into the genome of said host algae; d) Verifying the incorporation of the designer genes in the transformed algae with DNA PCR assays using the said PCR primers of the designer DNA constructs (FIGS. 3A and 3B); e) Measuring and verifying the designer algae features such as the inducible expression of the designer PSII-iRNA and $CF_1$-iRNA for enhanced photobiological $H_2$ production by assays of iRNA, PSII, $CF_1$, and $H_2$-production characteristics according to the specific designer features of the DNA constructs 300-A, 300-B (FIGS. 3A and 3B).

The above method for creating the designer transgenic algae to increase photobiological $H_2$ production efficiency can also be repeatedly applied for a plurality of operational cycles to achieve more desirable results. In various embodiments, any of the steps a) through e) 302, 304, 306, 312, 308, 310 of this method described above are adjusted to suit for certain specific conditions. In practice, any of the steps a) through e) 302, 304, 306, 312, 308, 310 of the method are applied in full or in part, and/or in any adjusted combination as well.

In various embodiments, the host organisms for transformation of the designer genes (FIGS. 3A, 3B, 3C, 3D) to create the transgenic designer photosynthetic organism are selected from the group that includes green algae, brown algae, red algae, blue-green algae, marine algae, freshwater algae, cold-tolerant algal strains, heat-tolerant algal strains, $H_2$-consuming-activity-deleted algal strains, uptake-hydrogenase-deleted algal strains, PSII-deficient algal strains, and combinations thereof. *Chlamydomonas reinhardtii* is a green alga that has had its genome sequenced. Therefore, it is a good model organism although the technology is applicable to any of the algae mentioned above for enhanced photobiological $H_2$ production. Proper selection of host organisms for their genetic backgrounds and certain special features is also beneficial. For example, the switchable PSII designer alga created from a cold-tolerant host strain, such as *Chlamydomonas* cold strain CCMG1619 that has been characterized to produce $H_2$ as cold as 4° C., enables the use even in cold seasons or regions such as Canada. Meanwhile, the switchable PSII designer alga created from a thermophilic photosynthetic organism, such as *Synechococcus bigranulatus*, enables use into the hot seasons or areas such as Mexico and the Southwestern region of the United States including Nevada, California, Arizona, New Mexico and Texas where the weather temperature can often be high. Furthermore, the switchable PSII designer alga created from a marine alga, such as *Platymonas subcordiformis*, enables using seawater, while the designer alga created from a freshwater alga, such as *Chlamydomonas reinhardtii*, uses freshwater.

Another feature is that various embodiments of the designer algae are devoid of any $H_2$-consuming activity that is not desirable for net $H_2$ production. That is, the switchable PSII designer algae will not consume any $H_2$ that it can produce. This feature, which further enhances the net efficiency for photobiological $H_2$ production, is incorporated by genetic inactivation or deletion of the $H_2$-consuming activity. The uptake hydrogenase activity is generally responsible for the $H_2$-consuming activity in algae. Therefore, this additional feature is incorporated by creating the designer algae from a host alga that has its uptake hydrogenase activity genetically deleted. Additional optional features of the designer algae include the benefits of reduced chlorophyll-antenna size which has been demonstrated to provide higher photosynthetic productivity and $O_2$-tolerant hydrogenase like the [NiFe] hydrogenases of *Ralstonia eutropha*, which can function under aerobic conditions. In various embodiments, these optional features are incorporated into the designer algae also by use of an $O_2$-tolerant hydrogenase and/or chlorophyll antenna-deficient mutant (e.g., *Chlamydomonas reinhardtii* DS521) as a host organism for gene transformation with the designer DNA constructs 300 (FIGS. 3A, 3B, 3C, 3D, 3E).

Examples of the designer PSII iRNA genes (DNA constructs) are shown in SEQ ID NOS: 1, 2, and 3. SEQ ID NO: 1 presents example 1 of a detailed DNA construct for a designer PSII/OEE1 suppressor gene (FIG. 3A) comprising: a PCR FD primer (sequence 1-20), a 282-bp HydA1 promoter (21-302), an Xho I NdeI site (303-311), an 405-bp antisense OEE1-iRNA sequence (312-716), an XbaI site (717-725), an RbcS2 terminator (726-940), and a PCR RE primer (941-967). This DNA construct (example 1) has been delivered into the nuclear genome of a *Chlamydomonas reinhardtii*-arg7 host cell using the techniques of electroporation and argininosuccinate lyase (arg7) complementation screening to create the switchable PSII designer alga. This designer gene is designed to encode a 405-bp antisense OEE1-iRNA to bind with the normal mRNA of OEE1, thus blocking (inhibiting) the translation of the mRNA into OEE1 protein. The expression of the PSII/OEE1-iRNA inhibitor is controlled by the use of the 282-bp HydA1 promoter. The RbcS2 terminator is used to properly terminate the transcription of the designer PSII/OEE1 suppressor gene to create an exact PSII/OEE1 iRNA as intended. The restriction sites (Xho I NdeI and XbaI site) are included to make the DNA construct into modular components so that each modular component could be flexibly taken out for modification and/or replacement. The PCR FD primer located at the beginning end and the PCR RE primer at the other end of the DNA construct (sequences 1-20 and 941-967) are selected from the sequence of a Human actin gene and can be paired each other. Blasting the sequences against *Chlamydomonas* GenBank found no homologous sequences of them. Therefore, they can be used for DNA PCR assays to detect and verify the designer PSII/OEE1-iRNA gene in a given transformant.

SEQ ID NO: 2 presents example 2 of a detailed DNA construct for a designer PSII/OEE1 suppressor gene (FIG. 3A) comprising: a PCR FD primer (sequence 1-20), a 282-bp HydA1 promoter (21-302), an Xho I NdeI site (303-311), an OEE1-iRNA sequence (312-1401), an XbaI site (1402-1410), an RbcS2 terminator (1411-1633), and a PCR RE primer (1634-1652). This designer PSII/OEE1-iRNA gene (example 2) is quite similar to example 1 (SEQ ID NO: 1), except that the designer OEE1-iRNA DNA is a 1090-bp long sequence (312-1401) that an antisenes foldable loop structure covers not only the 3 exons but also the 2 introns of the OEE1 gene. This designer PSII/OEE1-iRNA gene (SEQ ID NO: 2) has also been successfully delivered into the nuclear genome of a *Chlamydomonas reinhardtii*-arg7 host cell using the techniques of electroporation and argininosuccinate lyase (arg7) complementation screening to create the switchable designer alga.

SEQ ID NO: 3 presents example 3 of a detailed DNA construct for a designer PSII/OEE1 suppressor gene (FIG. 3A) comprising: a PCR FD primer (sequence 1-20), a 458-bp HydA1 promoter (21-478), a 569-bp OEE1-iRNA sequence (479-1047), an RbcS2 terminator (1048-1270), and a PCR RE primer (1271-1289). This designer PSII/OEE1-iRNA gene (example 3) is also similar to example 1, except that a 458-bp HydA1 promoter (21-478) is used and the OEE1-iRNA sequence (479-1047) is a 569-bp antisense DNA sequence of exon 1 and exon 2 for splicing of intron 2. This designer PSSI/OEE1 suppressor gene (SEQ ID NO: 3) has also been successfully delivered into the nuclear genome of an algal host cell to create the switchable PSII designer alga.

There are a number of embodiments for constructing the switchable PSII designer algae by creating and/or using a genetically transmittable factor that can inducibly or programmably control PSII activity. That is, to create and/or use a factor that can be genetically encoded to programmably control PSII activity to solve the $O_2$-related problems in photobiological $H_2$ production. An additional example on how to create the switchable PSII designer algae is described as follows. This example utilizes a hydrogenase promoter-linked streptomycin-production gene (FIG. 3C) to also create a switchable PSII designer alga for production of $H_2$ without the three oxygen-related problems. It has been demonstrated that streptomycin is an inhibitor to the synthesis of a key PSII component, the D1 protein. Without this D1 protein, PSII will no longer be able to perform photosynthetic water splitting to produce $O_2$. The gene for streptomycin biosynthesis has already been cloned. Therefore, it is now possible by application of synthetic biology techniques to use this streptomycin-production gene in conjunction with the hydrogenase promoter as a programmable switch to control PSII activity in photosynthetic organisms. FIG. 3C presents a DNA construct 300-C that can be genetically transferred into a host alga to create a switchable PSII designer alga with a phenotype similar to that illustrated in FIGS. 4A and 4B. That is, this designer alga containing the DNA construct 300-C can also grow and accumulate organic reserves (such as starch) by autotrophic photosynthesis using $CO_2$ under aerobic conditions, such as in an open pond (FIG. 4A). When the algal culture is grown and ready for $H_2$ production, the streptomycin-production gene 314 is then expressed simultaneously with the induction of the hydrogenase enzyme under anaerobic conditions. The expression of the streptomycin-production gene 314 inhibits the synthesis of the D1 protein, thus leading to gradual inactivation of PSII $O_2$ evolution and activation of $H_2$ production without $O_2$ production (FIG. 4B).

Figure 4C:
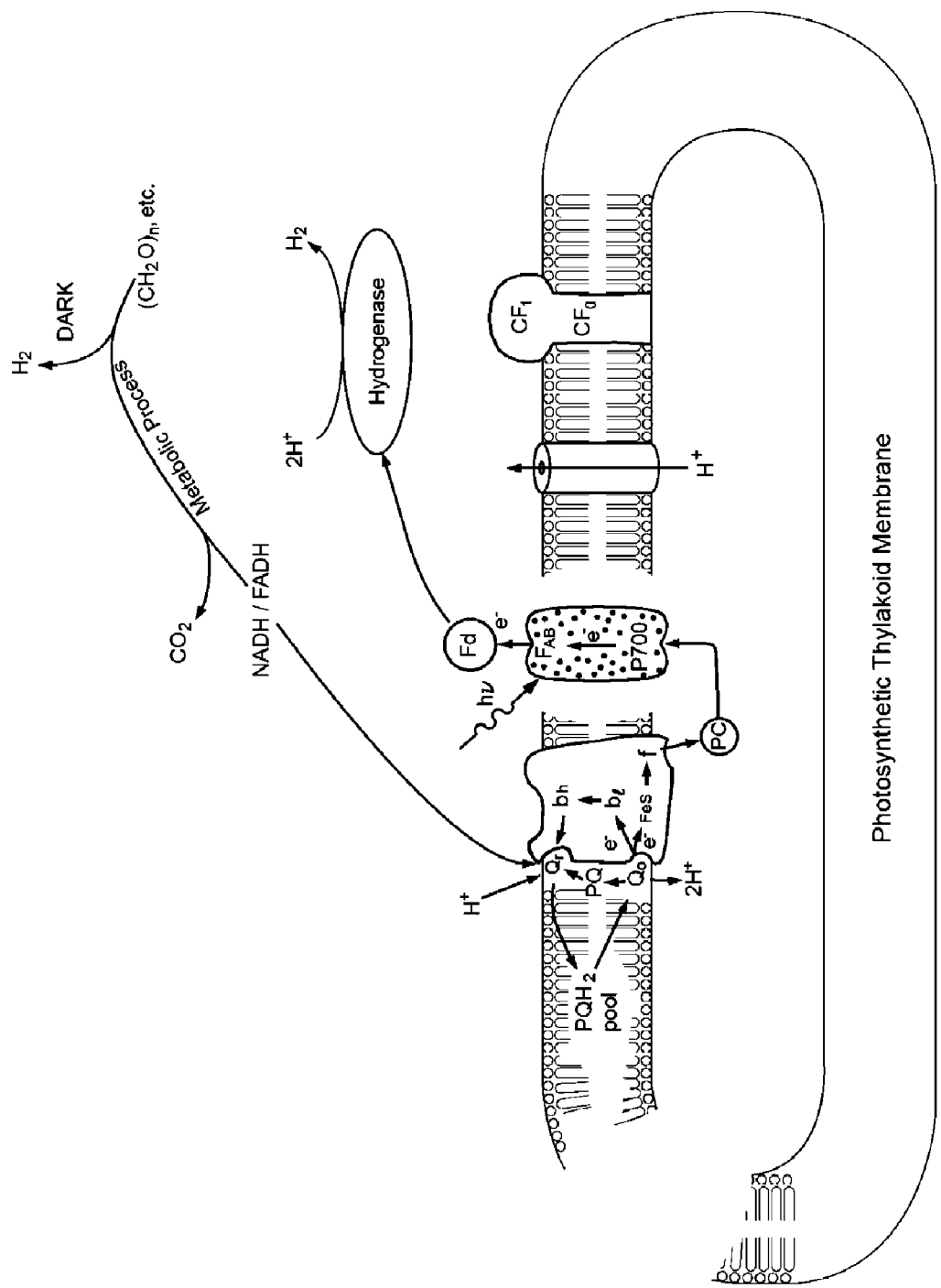
FIG. 4C illustrates the photobiological $H_2$ production pathway in a switchable-PSII designer alga when the designer PSII-suppressor (and/or inhibitor) gene and the designer proton-channel producing gene are expressed upon induction of the hydrogenase.

Another aspect is the combination of switchable PSII with programmable proton channel and additional features. In one embodiment, it is a preferred practice to apply the feature of the switchable PSII in combination with the benefits of creating a free proton channel in algal photosynthetic thylakoid membrane (FIG. 4B). Proton channels are created not only by selectively suppressing the expression of $CF_1$ (FIG. 4B) using a designer CF1-iRNA gene (FIG. 3B), but also, in another embodiment, by targeted genetic insertion of proton channels such as polypeptide (or protein) pores into algal photosynthetic thylakoid membrane (FIG. 4C) using a designer proton-channel gene (FIG. 3D). The detailed arts for targeted genetic insertion of proton channels into algal photosynthetic membrane have now been reported by this inventor in a separate patent application for a different invention. Some of the arts can be used here as an optional method to create proton channels in algal photosynthetic thylakoid membrane under $H_2$-producing conditions (FIG. 4C). Briefly, as shown in the DNA construct 300-D of a designer proton-channel gene (FIG. 3D), a designer proton-channel producing gene 318 is used with a targeting sequence 316 and an inducible promoter 304, such as a hydrogenase promoter. The molecular structure (and thus the DNA sequence) of a polypeptide proton channel is designed according to certain natural proton-channel structures at nanometer scale: melittin, gramicidin, $CF_o$ protein (the proton channel of chloroplast coupling factor $CF_oCF_1$), $F_o$ protein (the proton-channel structure of mitochondrial coupling factor $F_oF_1$), and their analogs. Since it is a beneficial to keep the capability of recyclable grow for a switchable PSII designer, accomplishing targeted insertion of the designer proton channels specifically into algal thylakoid membrane (so that the remaining parts of a designer alga cell including its mitochondria and cell membrane are kept intact) is important here. Therefore, in one embodiment, it is a preferred practice to properly select and/or design the targeting DNA sequence to guide the insertion of proton channels into algal photosynthetic thylakoid membrane along the induction of the hydrogenase. The targeting sequences that can be used and/or modified for this purpose include (but are not limited to) the transit-peptide sequences of: plastocyanin apoprotein (Pcy1), the LhcII apoproteins, OEE1 apoprotein (PsbO), OEE2 apoprotein (PsbP), OEE3 apoprotein (PsbQ), hydrogenase apoproteins (such as Hyd1), PSII-T apoprotein (PsbT), PSII-S apoprotein (PsbS), PSII-W apoprotein (PsbW), $CF_oCF_1$ subunit-γ apoprotein (AtpC), $CF_oCF_1$ subunit-δ apoprotein (AtpD), $CF_oCF_1$ subunit-II apoprotein (AtpG), photosystem I (PSI) apoproteins (such as, of genes PsaD, PsaE, PsaF, PsaG, PasH, and PsaK), Rubisco SSU apoproteins (such as RbcS2), chloroplast transit-peptide sequences of nuclear genes, and/or their analogs and modified designer sequences.

The benefits of a proton channel created with a designer proton-channel producing gene (FIG. 3D) are similar to those created with a designer $CF_1$-iRNA gene while the features of the switchable PSII created with a designer PSII-iRNA gene are also similar to those created with a designer streptomycin (PSII inhibitor) producing gene. Therefore, in various embodiments, these four types of designer genes (FIGS. 3A, 3B, 3C, and 3D) are applied in various combinations to create the switchable PSII designer algae that also combine with the benefits of a free proton channel in algal photosynthetic thylakoid membranes under $H_2$-producing conditions as shown in FIGS. 4B and 4C. This combination of benefits is also achieved by algal hybridization of a switchable PSII designer alga with another transformed alga that contains a designer proton-channel gene (FIG. 3B or 3D), in addition to transformation of a designer proton-channel gene using a switchable PSII designer alga as a host organism.

As mentioned previously, operation of the PSI-driven $H_2$-production mechanism results in translocation of protons across thylakoid membrane from the stroma into the lumen as the reducing power (NADH, NADPH, and FADH) from degradation of organic reserves enters the PQ pool near the $Q_r$ site of Cyt b/f complex and is then oxidized at the $Q_o$ site. If a free proton-conducting channel does not exist, protons could accumulate inside the thylakoids and impede the electron transport for this PSI-driven $H_2$ production. Use of a free proton-conducting channel eliminates the restriction of photosynthetic $H_2$ production by proton accumulation (problem 4). Furthermore, the presence of a free proton-conducting channel in algal thylakoid membrane also ensures the needed inactivation of the Calvin-cycle activity (which is associated with problems 5, 6, and 1) so that $CO_2$ and/or $O_2$ no longer act as a terminal electron acceptor through the Calvin-cycle activity to compete with the Fd/hydrogenase $H_2$-production pathway for the electrons derived from the PSI-driven decomposition of the organic reserves. Consequently, incorporation of a proton channel helps eliminate the four proton-gradient-related problems (1, 4, 5, and 6), while use of the switchable PSII solves the three $O_2$-related problems (1, 2, 3). Therefore, the combination of a switchable PSII with a proton channel in the switchable PSII designer alga (FIGS. 4B and 4C) ensures to solve all the six technical problems that currently challenge those in the field of photobiological $H_2$ production: (1) drainage of electrons by $O_2$, (2) poisoning of the hydrogenase enzyme by $O_2$, (3) the mixed $H_2$ and $O_2$ gas-product separation and safety issues, (4) restriction of photosynthetic $H_2$ production by accumulation of a proton gradient, (5) competitive inhibition of photosynthetic $H_2$ production by $CO_2$, and (6) requirement for bicarbonate binding at photosystem II (PSII) for efficient photosynthetic activity.

Figure 5:
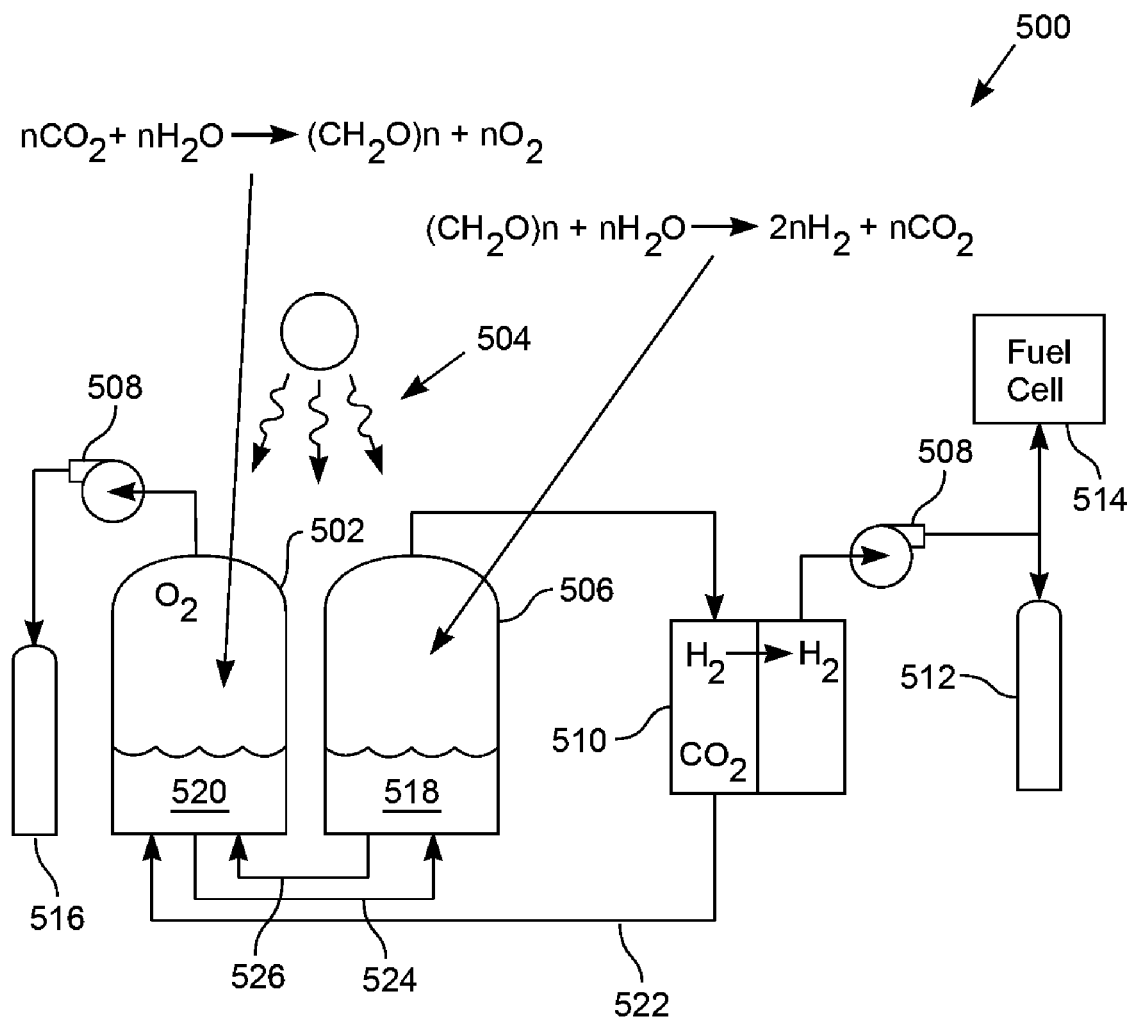
FIG. 5 illustrates one embodiment of a photo-bioreactor and gas-product separation and utilization system.

The various embodiments further teach how the switchable PSII designer algae are used with a photo-bioreactor and gas-product separation and utilization system 500, as illustrated in FIG. 5, for enhanced photobiological $H_2$ production. FIG. 5 illustrates one embodiment of a system 500 that includes an aerobic reactor 502 connected to an anaerobic reactor 506. The aerobic reactor 502 contains a quantity of algal culture 520 in aerobic conditions. The anaerobic reactor 506 contains a quantity of algal culture 518 in anaerobic conditions. Both the aerobic reactor 502 and the anaerobic reactor 506 are exposed to light 504, such as sunlight. The $CO_2$ and $H_2$ produced in the anaerobic reactor 506 are pulled through a $H_2$ separation membrane 510 by a vacuum pump 508. The $CO_2$ on one side of the membrane 510 is transferred to the aerobic reactor 502 via line 522. The $H_2$ on the opposite side of the membrane 510 is transferred to a $H_2$ storage tank 512 and the fuel cell 514. The algal culture 518 in the anaerobic reactor 506 is transferred to the aerobic reactor 502 via line 526 when the algal culture 518 is exhausted. The algal culture 520 in the aerobic reactor 502 is transferred to the anaerobic reactor 506 via line 524 when the algal culture 520 is ready for $H_2$ production. Those skilled in the art will recognize that other configurations of a system 500 can be implemented without departing from the spirit and scope of the present invention A single-organism (switchable PSII designer alga) two-stage $H_2$-production technology is illustrated. In the illustrated single-organism-two-stage $H_2$-production system 500, organic reserves, such as starch, are accumulated through photoautotrophic algal culture growth by normal oxygenic photosynthesis using $CO_2$ and sunlight energy 504 in an aerobic reactor 502 where $CO_2$ and $H_2O$ are converted into biomass materials such as starch $[(CH_2O)_n]$ by the normal autotrophic photosynthesis as illustrated in FIG. 4A:

$$nCO_2 + nH_2O \rightarrow (CH_2O)_n + nO_2 \quad (1)$$

When the algal culture 520 is grown and significant amounts of organic reserves are accumulated in the designer algal cells, the culture 518 is then placed under anaerobic conditions after flowing into an anaerobic reactor 506 so that the inducible promoter (such as hydrogenase promoter)-linked designer gene (FIG. 3A or 3C) of PSII suppressor (inhibitor) [such as a PSII iRNA or streptomycin] will then be expressed, simultaneously upon the induction of the hydrogenase enzyme. As illustrated in FIG. 4B, the expression of the PSII inhibitor gene will shut off PSII $O_2$-evolution activity so that the alga will produce $H_2$ by the metabolic (dark) and PSI-driven (light) $H_2$ production pathways without production of $O_2$ with the following process reaction:

$$(CH_2O)_n + nH_2O \rightarrow 2nH_2 + nCO_2 \quad (2)$$

The source of electrons for the metabolic and PSI-driven $H_2$ production is organic reserves, such as starch (FIG. 4B) that are made in the previous cycle of oxygenic photosynthetic $CO_2$ fixation (FIG. 4A). Since the gas product in this case (FIG. 4B) is essentially pure $H_2$ and $CO_2$ without $O_2$ because of the inactivation of PSII $O_2$-evolution activity, a $O_2$-free condition in an algal bioreactor can now be easily maintained for $H_2$ production—all of the three $O_2$-related problems (including problems 1-3: drainage of electrons by $O_2$, poisoning of the hydrogenase enzyme by $O_2$, and the gas-separation and safety issues) are thus eliminated. This algal $H_2$-production system 500 does not require an $O_2$-tolerant hydrogenase, neither does it require a $H_2$-$O_2$ gas-separation process. Consequently, the algal $H_2$-production process becomes more stable and efficient because both the drainage of electrons by $O_2$ and poisoning of the hydrogenase enzyme by $O_2$ does not occur with the designer algae.

In the anaerobic reactor 506, a designer proton-channel producing gene (FIG. 3D) and/or designer $CF_1$-suppressor gene (FIG. 3B) incorporated into the switchable PSII designer alga is expressed to create a free proton channel in algal photosynthetic thylakoid membrane along with the expression of the PSII suppressor gene upon induction of the hydrogenase. As shown in FIGS. 4C and/or 4B, the expression of a free proton channel in the algal photosynthetic thylakoid membrane greatly facilitates the needed flow of protons across the thylakoid membrane to further enhance the photobiological $H_2$-production process.

According to the process reaction (2), the ratio of $H_2$ to $CO_2$ in the gas products should be about 2:1. That is, under an idealized condition, the gas products from the photobiological $H_2$-production process in the anaerobic reactor 506 consists of about 67% $H_2$ and 33% $CO_2$. As shown in FIG. 5, the pure $H_2$ and $CO_2$ gas products from this photobiological $H_2$-production process in the anaerobic algal reactor is easily collected, separated, and stored/utilized with available engineering technologies including pipe lines with a pump 508 and nanometer-membrane gas separation system (or a commercial pressure-swing gas-separation system) 510 for separation of $H_2$ from $CO_2$. It is worthwhile to note that the $H_2$ gas product from the photobiological $H_2$-production process is completely free of carbon monoxide (CO) because there is absolutely no mechanism (no CO-producing enzyme) for any CO generation in the algae. The $H_2$ gas product from this process is enzymatically pure, which is perfect for fuel-cell 514 applications. Therefore, the $H_2$ gas product from this process can be immediately used by fuel-cell 514 operations to generate electricity and/or collected into storage tanks/hydrides 512 for cash sales. In the illustrated embodiment, the $CO_2$ gas product is fed into the algal culture medium 520 for photosynthetic conversion back into biomass in the aerobic reactor 502. In various embodiments, the $O_2$ gas product from the aerobic algal reactor 502 is collected in a tank 516 or vented into the atmosphere.

The ideal net result of the single-organism (switchable PSII designer alga) two-stage $H_2$-production technology is the conversion of $2nH_2O$ to $2nH_2$ and $nO_2$ as a result of the summation of the two process reactions (1 and 2). That is, the net result is the production of hydrogen and oxygen from water with no $CO_2$ emission. The maximal theoretical sunlight-to-$H_2$ energy conversion efficiency for this single-organism-two-stage $H_2$-production system 500 is estimated to be about 5%.

Another feature is that the designer alga provides the capability for repeated cycles of photoautotrophic culture growth (starch accumulation) under normal aerobic conditions in an aerobic reactor 502 (FIG. 4A) and efficient production of $H_2$ under anaerobic conditions in an anaerobic reactor 506 (FIG. 4B). The switchable-PSII designer alga contains normal mitochondria, which uses the reducing power (NADH) from organic reserves (and/or exogenous substrates, such as acetate) to power the cell immediately after its return to aerobic conditions. Therefore, when the algal cell is returned to aerobic conditions (aerobic reactor 502) after its use under anaerobic conditions (anaerobic reactor 506) for production of $H_2$, the cell will stop suppressing PSII activity in thylakoid membranes and start to restore its normal photoautotrophic capability by synthesizing functional thylakoids. Consequently, it is possible to use this type of genetically transformed organism for repeated cycles of photoautotrophic culture growth (starch accumulation) under normal aerobic conditions in an aerobic reaction (FIG. 4A) and efficient production of $H_2$ under anaerobic conditions in an anaerobic reactor 506 (FIG. 4B). That is, this photobiological $H_2$-production technology is operated continuously by circulating rejuvenated algal culture 520 from the aerobic reactor 502 into the anaerobic reactor 506 while circulating the used algal culture 518 from the anaerobic reactor 506 (after its use for $H_2$ production) into the aerobic reactor 502 for rejuvenation by synthesizing functional thylakoids and accumulating organic reserves (starch) through photosynthetic $CO_2$ fixation.

There are additional ways that the switchable PSII designer algae can be used. For example, the used algal culture from the anaerobic reactor 506 does not have to be circulated back to the aerobic reactor 502. Instead, the used algal culture is taken out to be used as fertilizers or biomass feed stocks for other processing because the photoautotrophic growth of the designer switchable PSII designer alga in an aerobic reactor 502 continuously supplies algal cells to an anaerobic reactor 506 for the photobiological $H_2$ production (FIG. 5). Another way is to use switchable PSII designer algae as biocatalysts to produce $H_2$ from organic substrates. This is done by adding organic substrates, such as acetate, organic acids, ethanol, methanol, propanol, butanol, acetone, carbohydrates, lipids, proteins, biomass materials, and combinations thereof, for quick photoheterotrophic growth in an aerobic reactor 502 and for photobiological $H_2$ production in an anaerobic reactor 506.

There are additional embodiments that the switchable PSII designer algae is created and used. For example, in yet another embodiment, the switchable PSII designer algae is created by transformation of a PSII-deficient mutant using a complementary designer inducible promoter-linked PSII-producing gene 320 (illustrated in FIG. 3E). Many PSII-deficient or deletion mutants that lack certain PSII component(s) may be selectively used as a host organism to create the designer algae in this manner as well. Examples of PSII-deficient mutants that may be used as a host organism for creation of the said designer algae include, but are not limited to, an OEE1-deficient mutant, a D1-deficient mutant, a CP47-deficient mutant, a CP43 deficient mutant, and/or a D2-deficient mutant. The PSII genetic switch here is a designer PSII (e.g., OEE1) producing gene (FIG. 3E) that switchably restores the PSII (e.g., OEE1) function in a corresponding complementary PSII (e.g., OEE1) deficient mutant. The DNA construct 300-E of a designer PSII gene (FIG. 3E) is similar to that of FIG. 3A, except that a PSII encoding gene which complements the specific PSII deficiency is used instead of using a PSII iRNA (suppressor) sequence 306. Examples of a PSII encoding sequence 320 for a designer PSII gene (FIG. 3E) includes, but are not limited to, the DNA sequences that can encode for an OEE1, a D1, a CP47, a CP43, and/or a D2 protein subunit that specifically complements its corresponding PSII deficiency in an OEE1-deficient mutant, a D1-deficient mutant, a CP47-deficient mutant, a CP43 deficient mutant, and/or a D2-deficient mutant. In one embodiment, the inducible promoter 304 for a designer PSII gene (FIG. 3E) is a promoter that is induced under aerobic conditions, such as the nitrate reductase (Nia1) promoter. This type of switchable PSII designer algae can also be combined with the feature of inducible creation of free proton channels in algal thylakoid membrane using a designer proton channel gene, such as that of FIG. 3B and/or FIG. 3D. In one embodiment, the inducible promoter for a designer proton-channel producing gene (FIG. 3B or FIG. 3D) is an anaerobic promoter, such as a hydrogenase promoter. In this way, the designer alga that is created by genetic transfer of a designer proton channel gene (FIG. 3B or FIG. 3D) and a designer PSII (e.g., OEE1) gene (FIG. 3E) into a complementary PSII (e.g., OEE1) deficient mutant can be used for photobiological $H_2$ production. For example, the expression of an Nia1 promoter-linked designer OEE1 gene upon induction by addition of nitrate ($NO_3-$) fertilizer in the algal culture medium in an aerobic reactor 502 restores the OEE1 function in the OEE1 deficient mutant (host organism) so that the alga performs normal oxygenic photosynthetic $CO_2$ fixation and grows photoautotrophically just like the other type of PSII designer algae described previously (FIG. 4A). When the algal culture is grown and accumulates large amounts of organic reserves, such as starch, by the oxygenic photosynthetic $CO_2$ fixation, the algal cells are placed into an anaerobic reactor 506 where ammonium ($NH_4+$) fertilizer (but no $NO_3-$) is present. The presence of $NH_4+$ and the absence of $NO_3-$ inactivates the expression of the designer PSII (e.g., OEE1) gene because of the use of a nitrate reductase (Nia1) promoter, so that the PSII oxygen-evolution activity will gradually be inactivated. Meanwhile, the designer proton channel gene (FIG. 3B or FIG. 3D) is expressed in the anaerobic reactor 506 because of the use of an anaerobic promoter such as the hydrogenase promoter. The inactivation of the designer PSII (e.g., OEE1) gene expression and the activation of the designer proton-channel gene expression in the anaerobic reactor 506 results in a photobiological $H_2$ production mode that is similar to that illustrated in FIG. 4B and/or FIG. 4C, where pure $H_2$ and $CO_2$ are produced from organic reserves $[(CH_2O)_n]$ and water ($H_2O$) without the production of $O_2$. This teaches how a switchable PSII designer alga can also be created from a PSII-deficient mutant using a complementary designer PSII gene as a genetic switch and how this type of switchable PSII designer algae in combination with a designer proton-channel gene may be used also for enhanced photobiological $H_2$ production.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A transgenic alga comprising at least one exogenous transgene for providing a photosystem-II (PSII) function switch to increase the photobiological H$_2$ productivity of the transgenic alga relative to alga without the at least one exogenous transgene; wherein the at least one exogenous transgene comprises a nucleic acid construct having an externally inducible promoter; and a transcription terminator; the nucleic acid construct further comprises a polynucleotide sequence for a designer PSII-iRNA gene comprising a PSII iRNA sequence; and the polynucleotide sequence for a designer PSII-iRNA gene comprises SEQ ID NO: 1.

2. A transgenic alga comprising at least one exogenous transgene for providing a photosystem-II (PSII) function switch to increase the photobiological H$_2$ productivity of the transgenic alga relative to alga without the at least one exogenous transgene; wherein the at least one exogenous transgene comprises a nucleic acid construct having an externally inducible promoter; and a transcription terminator; the nucleic acid construct further comprises a polynucleotide sequence for a designer PSII-iRNA gene comprising a PSII iRNA sequence; and the polynucleotide sequence for a designer PSII-iRNA gene comprises SEQ ID NO: 2.

3. A transgenic alga comprising at least one exogenous transgene for providing a photosystem-II (PSII) function switch to increase the photobiological $H_2$ productivity of the transgenic alga relative to alga without the at least one exogenous transgene; wherein the at least one exogenous transgene comprises a nucleic acid construct having an externally inducible promoter; and a transcription terminator; the nucleic acid construct further comprises a polynucleotide sequence for a designer PSII-iRNA gene comprising a PSII iRNA sequence; and the polynucleotide sequence for a designer PSII-iRNA gene comprises SEQ ID NO: 3.

4. A transgenic alga with a genetic function switch to increase photobiological $H_2$ productivity, the transgenic alga comprising:
  a first exogenous transgene that encodes a proton channel configured to be inserted into a photosynthetic membrane of the transgenic alga;
  a first inducible promoter operatively linked to the first exogenous transgene such that the first exogenous transgene is induced under anaerobic conditions;
  a DNA sequence within the first exogenous transgene that targets insertion of the proton channel into a photosynthetic membrane of the transgenic alga;
  a second exogenous transgene that encodes a segment of iRNA that at least partially binds with an mRNA of at least one PSII functional enzyme such that a PSII system is downregulated; and
  a second inducible promoter operatively linked to the second exogenous transgene such that the second exogenous transgene is induced under anaerobic conditions;
  wherein the second exogenous transgene is selected from the group consisting of SEQ 1, SEQ 2, and SEQ 3.

* * * * *